United States Patent [19]
von Berg

[11] Patent Number: 5,374,401
[45] Date of Patent: Dec. 20, 1994

[54] BLOOD SAMPLING APPARATUS

[75] Inventor: Peter von Berg, Tiburon, Calif.

[73] Assignee: pvb medizintechnik gmbh, Eglharting, Germany

[21] Appl. No.: 80,333

[22] Filed: Jun. 22, 1993

[30] Foreign Application Priority Data

Jun. 22, 1992 [DE] Germany .............................. 4220309

[51] Int. Cl.⁵ .................................................. G01N 1/10
[52] U.S. Cl. ................................... 422/101; 128/760; 128/765; 73/863.71; 73/863.84; 73/864.13; 73/864.16; 422/100; 604/27; 604/38; 604/73
[58] Field of Search ............... 128/760, 763–766; 73/863.71, 863.81, 863.83, 863.84, 864, 864.13, 864.16; 422/99–102; 604/4–6, 27, 28, 36, 38, 43, 73

[56] References Cited

U.S. PATENT DOCUMENTS

| | | | |
|---|---|---|---|
| 2,851,036 | 9/1958 | Lipari | 128/765 |
| 4,580,577 | 4/1986 | O'Brien et al. | 128/760 |
| 4,673,386 | 6/1987 | Gordon | 604/48 |

FOREIGN PATENT DOCUMENTS

| | | | |
|---|---|---|---|
| 0301913 | 8/1988 | European Pat. Off. | A61B 5/14 |
| 0302752 | 2/1989 | European Pat. Off. | A61M 5/14 |
| 3428655 | 8/1984 | Germany | A61M 5/20 |
| 8801846 | 3/1988 | WIPO | A61B 5/02 |

Primary Examiner—James C. Housel
Assistant Examiner—David Redding
Attorney, Agent, or Firm—Ralph H. Dougherty

[57] ABSTRACT

A blood sampling apparatus includes a housing (1) closed off by a rotatable cover (4), which in turn seals off the housing completely with a seal (7). The cover has a threaded sleeve (9), which cooperates with a piston rod for axial displacement of a piston (2). The housing cover has an opening closed off by a sterile filter (11). When the piston (2) is displaced, this piston rod always remains completely inside the housing (1), so that no bacteria, other kinds of germs or any other kind of contamination can penetrate the housing from the outside (FIG. 1).

9 Claims, 4 Drawing Sheets

BLOOD SAMPLING APPARATUS

FIELD OF THE INVENTION

The present invention relates to an apparatus for sampling blood from a living being.

BACKGROUND OF THE INVENTION

Similar kinds of blood sampling devices are known from EP-A2-0 302 752 and WO 88/01846. When an infusion tube or a catheter has been inserted into a vein or artery of a patient, such as for a drip infusion and/or an indwelling direct blood pressure measuring device, and a blood sample is to be taken for analysis purposes, this sample is taken from the infusion tube at a point that is accessible from the outside. To this end, the apparatus of the prior art provide for sampling points, which are connected with a channel of the infusion system and are accessible from the outside by means of a plunger-type syringe.

Before blood can be sampled from this system, it must first be ensured that only undiluted blood of the patient is supplied, excluding any components of the infusion solutions or anticoagulants used for the purposes of direct blood pressure measurements. To this end, WO 88/01846 provides for two sampling points. The sampling point lying closer to the patient (anterior) is used for the actual withdrawal of the blood sample. The sampling point lying farther away from the patient (posterior) is used for temporary removal of infusion solutions from the system so that only undiluted blood is present at the anterior sampling point. Following withdrawal of the blood sample at the anterior sampling point, the quantity of infusion solution and blood taken at the posterior sampling point is reintroduced into the system.

With WO 88/01846, the removal and the reintroduction at the posterior sampling point are carried out by means of a conventional syringe, which has a needle that penetrates the otherwise impermeable seal plug. However, this involves complicated manipulation and entails the risk that contamination, germs and other morbific agents may enter the system through the injection needle. There is also the risk that hospital personnel can injure and infect themselves when they remove the needle; this has already led to a high number of hospital personnel being infected with AIDS.

It has been suggested to use a closed system that is not accessible from the outside when the posterior sampling point is designed as an indwelling intermediate accumulator equipped with a plunger/barrel arrangement and integrated into the infusion or catheter system (cf. brochure of the firm of Baxter, entitled "New Vamp; a closed system for easier, safer blood sampling from invasive lines" and the one of the firm of Pfrimmer Viggo GmbH & Co. KG entitled "Saw draw; geschlossenes Blutentnahmesystem mit Statham-Einmal-Druckwandler DTX/plus (i.e. Closed Blood Sampling System with Disposable Statham Pressure Transducer, DTX/Plus).

The sterility of the intermediate accumulator cannot always be guaranteed with these known blood sampling arrangements, particularly when blood is to be drawn from a patient a number of times one after the other. If a conventional plunger-type syringe is used, such as in WO 88/01846, bacteria and other kinds of germs can be entrained into the system when the plunger is pulled out of and then re-inserted into the cylinder or housing chamber.

OBJECT OF THE INVENTION

It is the object of the present invention to provide an improved blood sampling apparatus so that the intermediate accumulator used in blood sampling as a reservoir for quantities of blood mixed with infusion solutions and accumulated intermediately is absolutely sterile even when used more than once.

In the present invention, the intermediate accumulator is sealed against bacteria from the environment. When manipulated, no moving parts capable of entraining bacteria or other kinds of germs back into the system can get to the outside. Nevertheless, the system ensures an exchange of air that is necessary for displacement of the plunger. The invented apparatus is also easy to assemble and can be manufactured with only a few injection-molded parts.

A further advantage of the invention is that the apparatus is operated by turning the cap or cover, which facilitates manipulation, especially in conjunction with the turning limit stops. This ensures that the plunger is actually run fully down in the one limit position, so that the housing chamber is emptied completely. The seal between the cylinder or housing and the cap is preferably an annular seal for which an O-ring or the like can be used. This seal is easy to mount and can carry out its function with little engineering effort.

In one advantageous development of the invention, the cap is secured in the axial direction with respect to the housing by means of a snap closure. This obviates unintentional opening of the housing chamber, thus avoiding any contamination.

A further important advantage of the invention is that the plunger or piston, including its shaft or piston rod, is moved only within the housing; none of its sections exits the housing. This is achieved because the length of the threaded sleeve is at least the dimension of the displacement length of the plunger.

BRIEF DESCRIPTION OF THE DRAWINGS

The foregoing and other objects will become more readily apparent by referring to the following detailed description and the appended drawings in which.

DETAILED DESCRIPTION

Figure 1:
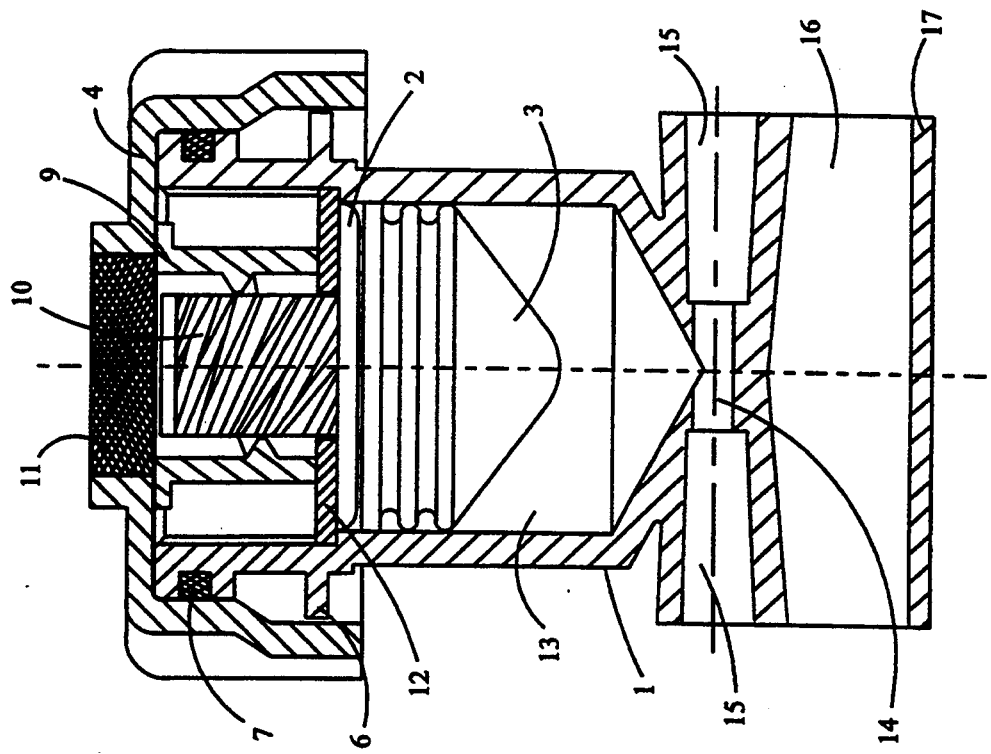
FIG. 1 is a cross-section through the blood sampling apparatus.
Figure 2:
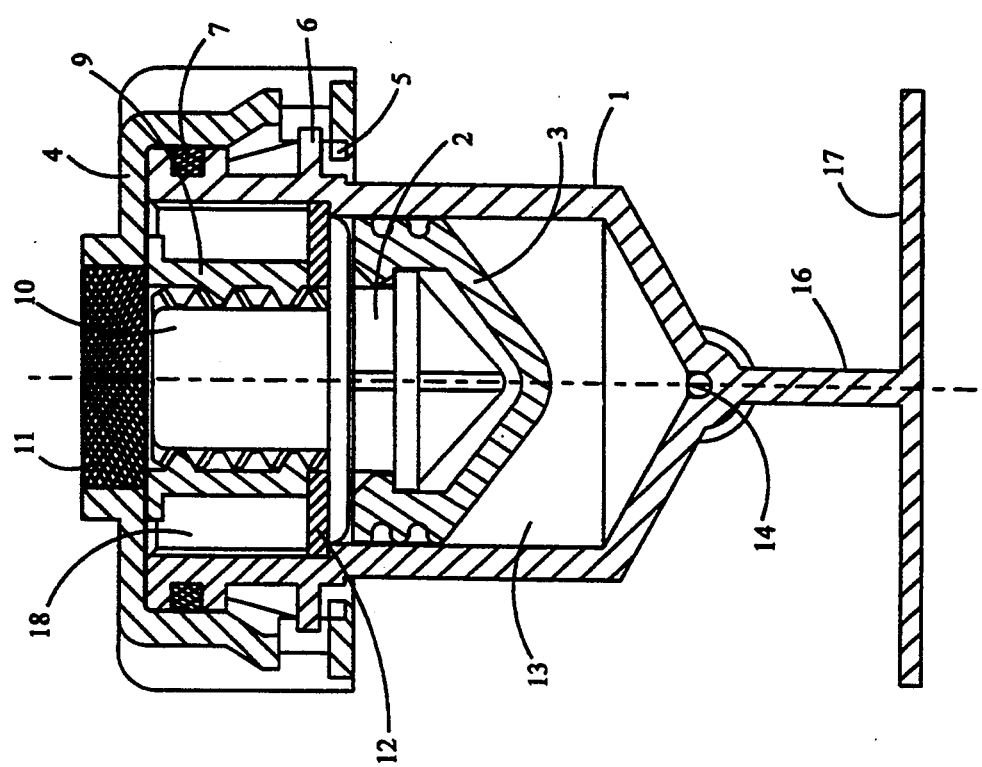
FIG. 2 is a cross-section through the blood sampling apparatus that is turned 90 degrees relative to that in FIG. 1.

FIG. 1 and 2 show the apparatus in the assembled condition. The apparatus has a cylinder or housing 1 in the interior of which a plunger or piston 2 is displaceably guided. The tip of the plunger 2 is surrounded by a plunger seal 3 made of flexible material, which seals off the plunger relative to the inner wall of the cylinder 1. The end of the cylinder that is open upwardly (according to the illustration in FIG. 1 and 2) is sealed with a cap or cover 4, which overlaps the opening end of the cylinder and can be locked on the cylinder by means of locking projections 5 overlapping an encircling shoulder 6, the cap 4 being turnable with respect to the cylinder 1.

Figure 3:
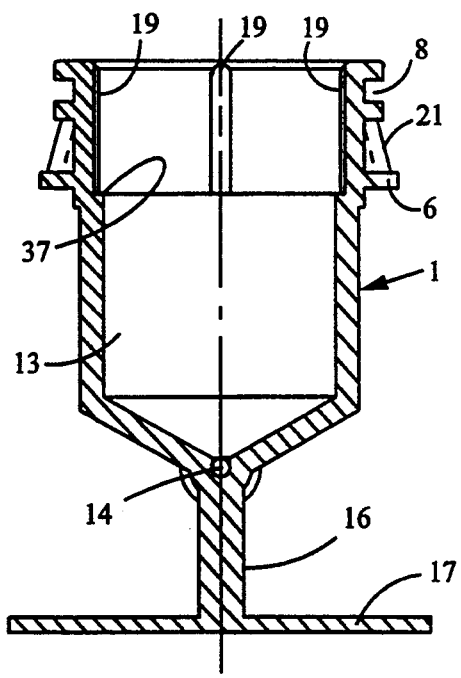
FIG. 3 and 4 are cross-sections through the cylinder of the blood sampling apparatus corresponding to FIG. 1 and 2.

A seal such as an O-ring 7, between the cylinder 1 and the cap 4 is held in a groove 8 (FIG. 3) on the outside of the cylinder.

The cap 4 has a threaded sleeve 9 that extends axially and has an internal thread with a relatively large degree of pitch. This internal thread cooperates with an outer thread on a shaft 10 of the plunger 2 so that the plunger is displaced in the axial direction when the cap 4 is turned with respect to the cylinder 1.

On its end face, the cap 4 has an opening into which a sterile filter 11 is inserted. This filter is permeable to air, but it is tightly impervious against bacteria, other types of germs and any other kinds of contamination.

An anti-twist protector 12 is provided so that the plunger 2 is only displaced linearly and does not turn when the cap 4 is turned.

The interior of the cylinder 1 is divided into two chambers by the plunger seal 3, that is, chamber 13, which is directly connected with a flow channel 14, and an upper venting chamber 18, which extends in the direction of the opening of the cylinder 1. This venting chamber 18 is also sealed off from the environment by means of the seal 7 as well as the sterile filter 11 when the plunger 2 is displaced. Hence, no bacteria, other kinds of germs or any other kind of contamination can penetrate the interior of the cylinder 1.

In the region of the flow channel 14, the cylinder changes its shape from cylindrical with truncated cone tip into an axially parallel web 16, ending at a second web 17 extending transverse thereto.

Figure 4:
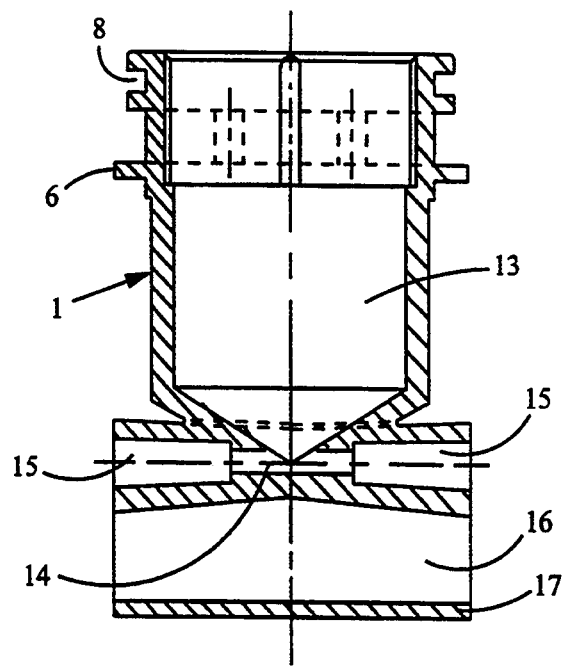
Figure 5:
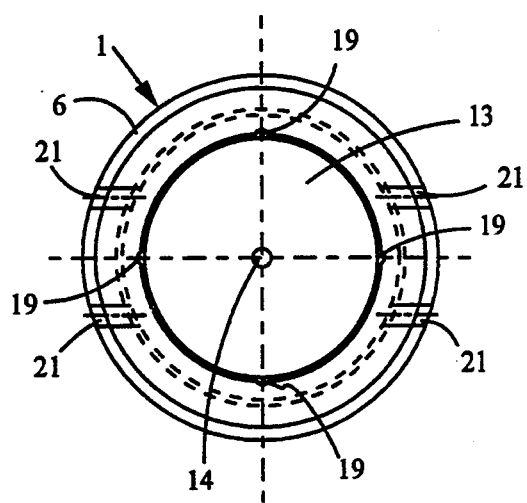
FIG. 5 is a plan view of the opening side of the cylinder in FIG. 3.
Figure 8:
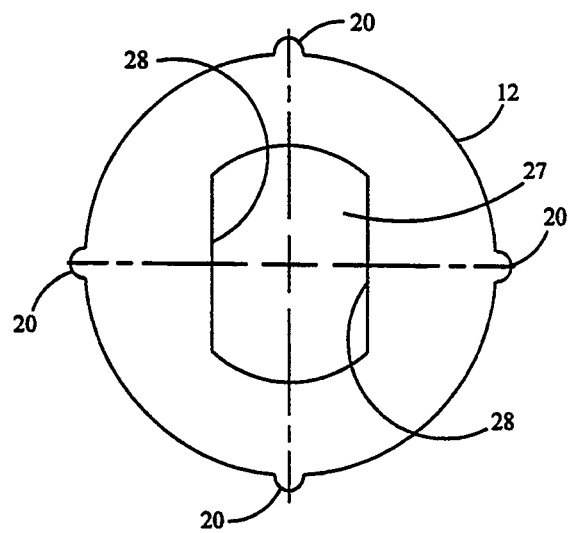
FIG. 8 is a plan view of an anti-twist protector used in the invention.
Figure 9:
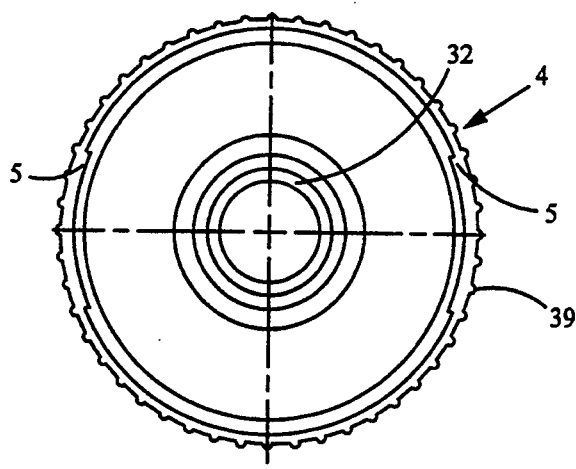
FIG. 9 is a plan view of the opening side of the cylinder cap.
Figure 10:
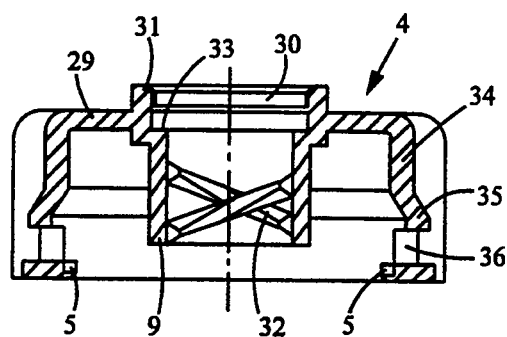
FIG. 10 and 11 are cross-sections of the cylinder cap corresponding to the views in FIG. 1 and 2.
Figure 11:
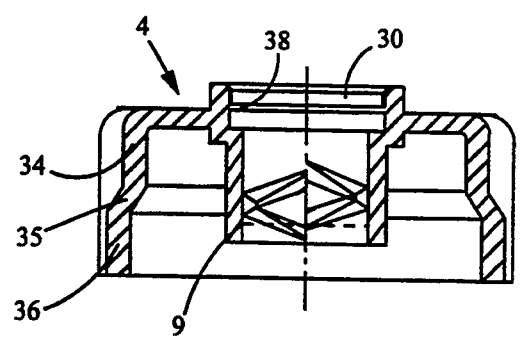
Figure 12:
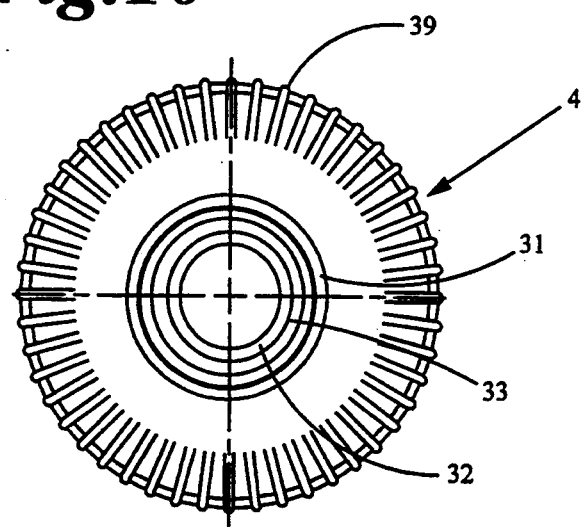
FIG. 12 is a view of the outside of the cylinder cap.

As can be seen in FIG. 2, the two ends of the flow channel 14 are enlarged into connections 15 to which the tubes can be connected. Further details of the cylinder 1 can be seen in FIGS. 3 to 5. Four axially extending grooves 19 used to guide the anti-twist protector 12 engaging these grooves with four corresponding projections 20 (FIG. 8) are provided in the inner wall of the cylindrical chamber 14 in the area directed toward the cap. The grooves 19 end at a shoulder 37 serving as an axial stop for the anti-twist protector 12.

The conical frustum end of the cylinder chamber 13 facing the flow channel 14 opens directly into the latter, that is, the tip of conical frustum inserted into this chamber would engage the flow channel 14. Since the plunger seal of the example embodiment shown in FIG. 1 and 2 has the appropriate shape, it is ensured that no fluid residue at all will remain in the cylinder chamber 13 when the plunger is pressed all the way down.

Four reinforcing ribs 21 connected to the shoulder 6 extend to a point close to the annular groove 8. These reinforcing ribs can also be used with a projection (not shown) of the cap 4 as a turn limiting stop. In addition, the side of the shoulder 6 facing away from the opening of the cylinder chamber 13 can have one or more turn limiting stops with a leading bevel and an indentation connected thereto engaged by the projections 5 in the stop positions.

Figure 6:
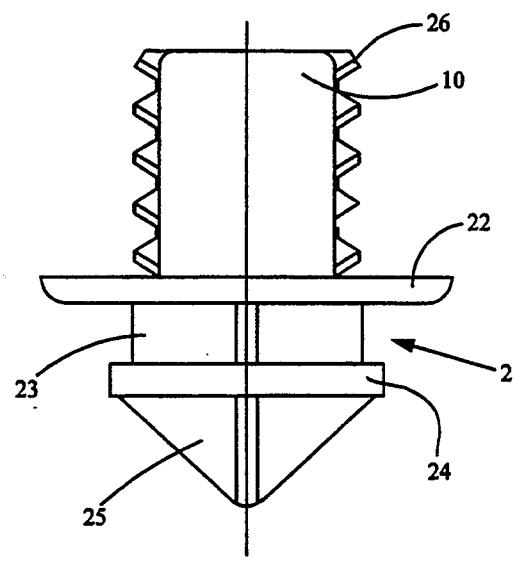
FIG. 6 is a side view of the plunger used in the invention.
Figure 7:
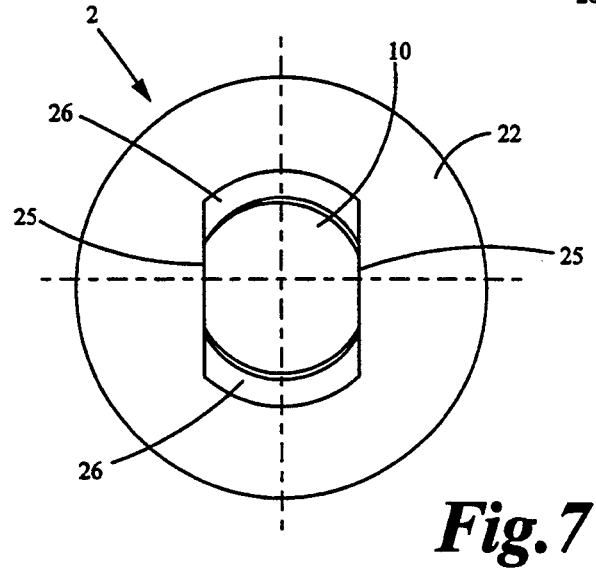
FIG. 7 is a plan view of the plunger looking toward the plunger shaft.

FIG. 6 and 7 give a more detailed view of the plunger 2 having a plunger shaft 10 with an external thread 26. This external thread 26 is followed by a radially projecting shoulder 22 having, with a certain amount of play, a diameter corresponding to the inside diameter of the cylinder chamber 13. This shoulder is followed by a section 23 with a smaller diameter that, furthermore, can consist only of two intersecting webs. This is in turn followed by a radially projecting shoulder 24 and then finally by a "conical or tapering" section 25, which in turn can only consist of two intersecting webs. The plunger seal 3 is held between the two shoulders 22 and 24 in both axial directions and is adjacent with its inner walling to the edge of the shoulder 24. The conical or tapering section 25 extends into a cavity of the plunger seal 3, and, when the plunger 2 is in the pressed-down condition, the tip of the conical or tapering section 24 is in contact with the inner walling of the corresponding conical or tapering tip of the plunger seal 3, thus forcing it into the flow channel 14.

As can be seen in FIG. 7, the plunger shaft 10 has two flattened sides 25, so that its thread 26 does not run completely around the periphery of the plunger shaft. The anti-twist protector 12 (FIG. 8), which is designed essentially as a flat disc, has a central opening 27, which fits the outline of the plunger shaft 10, and thus also has two opposing flattened sides 28. Hence, the plunger 2 cannot turn relative to the anti-twist protector. Since the anti-twist protector, for its part, is held by the projections 20 in the grooves 19 of the cylinder 1 so that it cannot twist, the plunger 2 can only move in the axial direction when the cap 4 is turned.

The cap is described in conjunction with FIG. 9 to 12.

The essentially flat wall 29 of the cap 4 pointing in an outward direction has a central opening 30 into which the bacteria filter 11 (FIG. 1) is inserted. A cylindrical section 31, which is used to hold and guide the bacteria filter 11 and which is set off from the wall 29, is adjacent to this opening. Starting at the inner side of the wall 19, the cylindrical section 31 is followed by the threaded sleeve 9, which has an internal thread 32 cooperating with the external thread 26 of the plunger shaft 10. The inside diameter of the threaded sleeve 9 is less than the diameter of the opening 30, so that a step 33 formed by this decrease in diameter serves as a support for the bacteria filter. Provided in the opening 30 is a rib 38 which extends radially inward and serves as an additional means to prevent the bacteria filter 11 from falling out.

The outer periphery of the wall 29 is followed by a cylindrical section 14 having a diameter corresponding to that of the side walls bounding the groove 8 of the cylinder 1, so that this section 34 takes over the sealing function in cooperation with the seal ring 7 (FIG. 1 and 2).

The cylindrical section 34 is followed by a widening section 35, which changes into the cylindrical section 36. The inside diameter of the cylindrical section 36 is somewhat greater than the outside diameter of the shoulder 6.

The radially inwardly extending locking projections 5, which grip behind the shoulder 6 and lock the cap with respect to the cylinder are formed in the cylindrical section 36. These locking projections 5 also serve as a turn limiting stop, as is described above in connection with the cylinder.

A milled, ribbed, or roughened edge 39 at the periphery of the cap 4 facilitates gripping and turning of the cap by hand.

What is claimed is:

1. Blood sampling apparatus comprising:
   a cylindrical housing closed at a first end, a flow channel communicating with said first end, and a displaceable piston situated in said housing;
   a cover (4) adapted to close a second end of said housing;
   sealing means (7) adapted to seal said cover to said housing, comprising an annular groove in the exterior of said housing and an annular seal ring (7) in said groove (8) in contact with the inner surface of said cover (4);
   said cover (4) having a depending central interiorly threaded sleeve (9), and an exteriorly threaded piston rod threadedly engaging and movable in said sleeve; and
   a bacteria filter permeable to air situated in the cover (4).

2. Blood sampling apparatus as described in claim 1, further comprising an anti-twist protector means (12) arranged inside said housing (1), which prevents turning of the piston (2) relative to the housing (1).

3. Blood sampling apparatus as described in claim 2, wherein said housing is provided with grooves, said anti-twist protector means being a flat disc (12) having projections positioned in said grooves (19) of the housing so it cannot turn, the anti-twist protector means (12) having a central opening (27) for passage of the piston rod, the central opening having a pair of opposing flattened sides (28), said piston rod (10) also having two corresponding flattened sides (25).

4. Blood sampling apparatus as described in claim 1, further comprising snap closure (5, 6) means for holding said cover in place axially on said housing.

5. Blood sampling apparatus as described in claim 4, wherein the said snap closure is formed by an annular shoulder (6) which projects radially from the housing, and locking projections (5) on the cover, which grip behind said shoulder (6).

6. Blood sampling apparatus as described in claim 1, further comprising turn limiting means (21) on said housing for limiting the turn of the cover.

7. Blood sampling apparatus as described in claim 2, wherein said anti-twist protector means (12) is fixed axially within the housing (1) between an end face of said threaded sleeve (9) and a shoulder (37) in said housing.

8. Blood sampling apparatus as described in claim 2, wherein the length of the threaded sleeve (9) is at least that of the displacement path of the piston (2).

9. Blood sampling apparatus as described in claim 1, wherein the end of the threaded sleeve (9) directed toward the second end of said housing is closed off by the bacteria filter (11).

* * * * *